United States Patent [19]

Allen et al.

[11] 4,041,089

[45] Aug. 9, 1977

[54] PROCESS FOR THE ISOMERIZATION OF DIMETHYLNAPHTHALENES USING A MORDENITE/ALUMINA CATALYST

[75] Inventors: John K. Allen, Batavia, Ill.; Ralph J. Bertolacini, Chesterton, Ind.

[73] Assignee: Standard Oil Company a corporation of Indiana, Chicago, Ill.

[21] Appl. No.: 700,323

[22] Filed: June 28, 1976

[51] Int. Cl.² ............................................... C07C 5/24
[52] U.S. Cl. ............................ 260/668 A; 260/668 F; 252/455 Z
[58] Field of Search ...................... 260/668 A, 668 F; 252/455 Z

[56] References Cited

U.S. PATENT DOCUMENTS

| 3,677,973 | 7/1972 | Mitsche et al. | 252/455 Z |
| 3,780,119 | 12/1973 | Shimada et al. | 260/668 A |
| 3,798,280 | 3/1974 | Shimada et al. | 260/668 F |
| 3,806,552 | 4/1974 | Oka et al. | 260/668 A |
| 3,888,938 | 6/1975 | Ogasawara et al. | 260/668 A |
| 3,930,987 | 1/1976 | Groud | 252/455 Z |
| 3,939,058 | 2/1976 | Plank | 252/455 Z |

*Primary Examiner*—Veronica O'Keefe
*Attorney, Agent, or Firm*—Robert E. Sloat; Arthur G. Gilkes; William T. McClain

[57] ABSTRACT

A process for the isomerization of 1,5 and 1,6-dimethylnaphthalenes to a product including 2,6-dimethylnaphthalene which comprises passing a feed stream containing the 1,5 and 1,6 isomers over a catalyst at isomerization reaction conditions which catalyst consists essentially of from about 35 to about 45 weight per cent of the hydrogen form of mordenite dispersed in an alumina matrix.

11 Claims, No Drawings

PROCESS FOR THE ISOMERIZATION OF DIMETHYLNAPHTHALENES USING A MORDENITE/ALUMINA CATALYST

BACKGROUND OF THE INVENTION

1. Field of the Invention

The field of art to which the present invention pertains is catalytic isomerization of dimethylnapthalenes. Relevant U.S. classifications where art may be found include U.S. Class 260-668(a) or 668(f).

2. Description of the Prior Art

U.S. Pat. No. 3,806,552 issued Apr. 23, 1974, relates to the vapor phase isomerization of dimethylnaphthalenes using a catalyst comprising 65 to 95 per cent by weight of a hydrogen from of mordenite in which about 80 per cent by weight of the metal cations are replaced with hydrogen ions, and 35 to 45 per cent by weight of an assistant catalyst selected from the group consisting of bentonite and fuller's earth.

Japanese Pat. No. 75 0059-357 issued May 22, 1975, relates to the isomerization of dimethylnaphthalenes by contacting a feed material with a mordenite catalyst containing one or more metals of chromium, molybdenum, and tungsten.

Japanese Pat. No. 75 0059-356 issued May 22, 1975, relates to the isomerization of dimethylnaphthalenes by contacting a feed mixture with a mordenite catalyst containing one or more ions of arsenic, bismuth, and antimony.

Japanese patent application No. 45-125543 filed Dec. 29, 1970, published Nov. 29, 1972, relates to isomerization of dimethylnaphthalenes using catalyst of mordenite and a carrier. Gamma alumina carriers are not recognized in this application.

U.S. Pat. No. 3,915,895 issued Oct. 28, 1975, relates to disproportionation of alkyl aromatic hydrocarbons in the presence of a catalyst which comprises the hydrogen form of mordenite and a group 1-B metal. The catalyst may also contain a group VI-B metal and can additionally be admixed with eta or gamma alumina. The catalytic properties of this catalyst, however, require that the specified metal or metals be placed on the catalyst.

U.S. Pat. No. 3,888,938 issued June 10, 1975, relates to liquid phase catalytic rearrangement of dimethylnaphthalenes by reacting those materials in the presence of a mixed catalyst which contains about 70 to 95 per cent by weight of the hydrogen form of mordenite which mordenite has at least 80 per cent by weight of the metal cations replaced with hydrogen ions, and from 30 to 45 per cent by weight of a promoter selected from the group consisting of bentonite and fuller's earth. The combination of the hydrogen form of mordenite was either bentonite or fuller's earth according to the teachings of this patent contribute to an improved isomerization process.

U.S. Pat. No. 3,798,280 relates to a process for isomerization and crystallization of dimethylnaphthalenes wherein the isomerization takes place using the hydrogen form of a mordenite which is generally in its pure form. There is no teaching or disclosure that the hydrogen from of mordenite can be mixed with any specified materials such as gamma alumina, and further more, no teaching that isomerization can be carried out in the absence of metallic components.

U.S. Pat. No. 3,851,002 issued Nov. 26, 1974, relates to a process for the isomerization of dimethylnaphthalenes in the gas phase by processing the feed materials over a silica-alumina catalyst having a specified particle size distribution.

U.S. Pat. No. 3,855,328 issued Dec. 17, 1974, relates to a process for the isomerization, transalkylation or disproportionation of alkyl naphthalene materials. Particular, alumino-silicate zeolites are used as the catalyst in such processing. The preferred zeolites have atomic ratios of aluminum to silica in the range of about one to one-tenth. A preferred zeolite is faujasite framework structure typically referred to as Linde type Y molecular sieves containing a specified rare earth cation such as cerium or lanthanum.

U.S. Pat. No. 3,780,119 issued Dec. 18, 1973, relates to a process for isomerization of dimethylnaphthalenes using a mordenite catalyst which contains at its ion exchangeable sites, a metal selected from the group consisting of lanthanum, sodium, potassium, magnesium, calcium, strontium, barium, aluminum, and zinc. The metal containing mordenite material is specifically disclosed as the primary catalytic agent in the process of this patent.

In a summary review of the prior art described, it can be concluded that there is no teaching or disclosure of the unique use of the hydrogen form of mordenite dispersed in a gamma alumina matrix. The specific claimed concentration of the hydrogen form of the mordenite in the alumina is not taught nor are the benefits relating to yield and catalyst life attributed to the specified mordenite concentration recognized.

SUMMARY OF THE INVENTION

The present invention can be summarized as a method for isomerization of dimethylnaphthalenes which comprises contacting a feed containing dimethylnaphthalenes with a catalyst consisting essentially of from about 35 to about 45 weight per cent of mordenite in the hydrogen form which is dispersed in an alumina matrix to effect the production of dimethylnaphthalene isomers.

In a broad embodiment our invention relates to a method for isomerization of dimethylnaphthalene including conversion of a feed containing 1,5-dimethylnaphthalene to 1,6-dimethylnaphthalenes, the process comprising contacting said feed at isomerization conditions with a catalyst consisting essentially of from about 35 to about 45 weight per cent of the hydrogen form of mordenite dispersed in an alumina matrix, to effect the production of said 1,6- and 2,6-dimethylnaphthalenes.

In a more preferred embodiment, our invention relates to a method for isomerization of dimethylnaphthalene including conversion of a feed containing 1,5-dimethylnaphthalene to 1,6- and 2,6-dimethylnaphthalene isomers, the process comprising said feed at isomerization conditions including the presence of a gaseous hydrogen and liquid feed with a catalyst consisting essentially of from about 35 to about 45 weight per cent of the hydrogen form of mordenite dispersed in a gamma-alumina matrix, to effect the production of said 1,6- and 2,6-dimethylnaphthalenes.

DETAILED DESCRIPTION OF THE INVENTION 2,6-dimethylnaphthalene (2,6-DMN) is an important precursor for the production of 2,6-naphthalenedicarboxylic acid, which itself can be used when reacted with polyols, alcohols or glycols for the production of high grade polyesters.

There are many methods to produce 2,6-DMN. One of the methods is the direct extraction of 2,6-DMN from refinery streams or coke-oven tar. This method is generally unattractive for many reasons including limited availability of 2,6-DMN from refinery sources and generally at very low concentrations. Eutectic formation between 2,6-DMN and 2,7-DMN prevents complete extraction of 2,6-DMN are, therefore, much more attractive.

One of the more attractive routes to the production of 2,6-DMN is via the isomerization of 1,5-DMN which itself is prepared by the selective synthesis from orthoxylene and butadiene. The 1,5-DMN product then can be isomerized to the desired 2,6-DMN isomer.

A major advantage of isomerization of 1,5-DMN is that it selectively avoids the difficult separation of 2,6-DMN and the 2,7-DMN isomers since the 2,6- and 1,6-isomers are the predominantly produced isomers.

The catalyst of the present invention comprises a material consisting essentially of from about 35 to about 45 weight per cent of mordenite in the hydrogen form, and from aobut 55 to about 65 weight per cent of alumina, preferably gamma-alumina. Specifically, the mordenite is present evenly distributed through the alumina, the latter present as a matrix.

Mordenites are well-known in industry as possessing various catalytic properties. In accordance with the use of mordenite in the catalyst claimed herein, it is especially preferred that the mordenite be essentially 100 per cent decationized, that is, essentially all of the exchangeable cation sites in the mordenite crystal structure have been replaced with hydrogen ions. An eminently suitable source of synthetic mordenite material is the material produced by the Norton Company having a tradename Zeolon 200. This material is a hydrogen form of mordenite in which the metal cations in the crystal structure of the mordenite material have been replaced by hydrogen either by use of ammonium hydroxide exchange or dilute hydrochloric acid contact. Susequent heating of the material to drive off either ammonia or the removal of solium or metallic chloride results in the hydrogen form mordenite product. In a preferred instance, the mordenite used herein is essentially 100 per cent hydrogen form where, to the extent practicable, essentially all of the metal cations in the exchangeable sites in the crystal structure of the mordenite have been substituted by hydrogen ions.

Naturally occurring mordenites may also be used in this invention. In certain instances, it may be necessary to acid etch the mordenite to alter its $SiO_2$ to $Al_2O_3$ ratio.

The mordenite material is evenly dispersed in a matrix of alumina. Specifically, the alumina which can be used include materials such as gamma alumina, eta alumina, or other similar commercially available alumina materials. Especially preferred is gamma alumina because of its availability and ease of processing into finished product.

In producing the claimed catalyst a dried powder of Zeolon 200 from the Norton Company can be placed in an alumina sol. The alumina sol and mordenite mixture is mixed and then by a change in pH, generally by the addition of ammonia or ammonium hydroxide, the mixture solidifies. It is then dried and extruded or pelletized into small particles which contain the appropriate quantities of the hydrogen form of the mordenite evenly distributed in the alumina matrix.

In a expecially preferred instance, the finished catalyst contains from 35 to 45 weight per cent of the hydrogen form of mordenite, the remaining material consisting essentially of the gamma alumina matrix. It is especially preferred that no other catalytic materials be present in the catalyst other than in trace quantities, and preferably, in noncatalytic amounts. Binders, mold lubricators, etc., may be incorporated into the catalyst, however.

Calcination of the catalyst particles may take place for activation or for removal from the particles or both. Steam treatment of the finished catalyst may also take place.

As is illustrated in the examples below, a catalyst comprising essentially 100 per cent mordenite has a much reduced catalyst life and ultimate yield of 2,6-DMN produced from a base feedstock. When testing a catalyst which contained 2.4 weight per cent of hydrogen form of mordenite dispersed in a gamma alumina matrix, relatively short catalyst lives were obtained, and the ultimate yields of the 2,6-DMN isomer were substantially reduced as compared to the process which utilized the preferred catalyst composition.

A preferred composition containing 40 weight per cent of hydrogen from of mordenite with the remaining material consisting essentially of the gamma alumina matrix showed excellent catalyst life while also attaining increased yields of the 2,6-DMN isomer as compared to runs of similar conditions.

It is surprising that the present catalyst works especially in the absence of other well-known active isomerization components (e.g. rare earth or other metals) especially those described in the prior art section of this application.

Isomerization conditions generally include either gas or liquid phase operations. However, it is preferred to operate liquid phase operations as opposed to the gas phase operations since longer catalyst life results from the use of the liquid phase conditions. This is most probably a result of the liquid material contacting the catalyst and washing coke or heavy carbonaceous materials from the catalyst. In the gaseous phase isomerization conditions, very little, if any, washing effects would occur.

Isomerization conditions incude reactor temperatures anywhere in the range of from about 200° to 400° C. or higher. Preferred temperatures are in the range of from about 250° to about 350° C., and especially preferred temperature around 300° C. Pressures can vary depending upon whether gaseous or liquid phase operations within the isomerization reaction zone are to take place. Specifically, pressures can vary anywhere from around atmospheric to 1500 psig or higher. In many instances, it is possible to operate a liquid phase operation at a pressure somewhere around 50 psig. Weight hourly velocities of the 1,5-DMN fed to the reaction zone can vary anywhere from less than 0.1 per hour up to 1.0 per hour or higher. Especially preferred for liquid phase operations includes weight hourly velocities of about 0.25 per hour.

In operations in which hydrogen is desired to be passed into the reaction zone along with feed, the mole ratio of gaseous hydrogen to the 1,5-DMN fed to the reaction zone can vary anywhere from less than about 0.01 to about 1.0 or higher. It is especially preferred that the hydrogen to 1,5-DMN mole ratio be somewhere from about 0.1 to 0.4 with the 0.2 being an especially preferred value.

It is contemplated that recycle operations can take place. After the conversion of the feed a recovery operation can take place in which the preferred isomer (2,6-DMN) is recovered, and much of the remaining effluent material can be recycled to the reaction zone combined with the fresh feed. Under such recycle conditions, it is contemplated that per pass conversion and yields will not be as high as would necessarily be expected during once through operations since most of the unreacted feed leaving the reaction zone can be recycled to extinction.

Separation and recovery of the preferred 2,6-DMN isomer can take place by appropriate crystallization techniques with return of undesired isomers to the reaction zone.

Reactor designs are generally well-known in the art and may be up flow or down flow depending upon the specific preference for the operator.

When referring to gaseous operations, we generally mean the passage of vaporous hydrocarbon feed together with gaseous hydrogen through the reaction zone at conditions so that generally all, and preferably, essentially all of the material fed to the reaction zone enters and leaves such zone in a vapor phase. The vapors leaving as effluent from the reaction zone can be condensed by any of well-known means and the liquids thereafter treated for recovery of the preferred DMN isomer.

In some instances, liquid phase operations can take place. For the present and inventive concept, a liquid phase operation is especially preferred, because of longer catalyst life together with some increase in yield of 2,6-DMN isomer. Liquid phase operations can be performed under either liquid full or trickle operations. Liquid full operations include conditions in which the feedstock enters and leaves the reaction zone as a liquid with the reaction zone itself essentially totally full of liquid during isomerization. Typically, liquid full isomerization reaction conditions will take place by passing a liquid feed (in some instances along with gaseous hydrogen) into the bottom of a reaction zone and recovering effluent from the top of the reaction zone. In this instance, the entire reaction zone would be filled with liquid feed. There are certain disadvantages to this type of operation. In many instances, the residence time of the feed in the reaction zone is excessive producing large quantitites of undesirable side products in the reaction zone.

The preferred reaction mode is the trickle-bed operation. In this case, liquid feed together with gaseous hydrogen is passed into the top of the reaction zone and allowed to pass in a downward direction through the catalyst bed. The reacted feed is recovered as a liquid at the bottom of the reaction zone.

In this type of operations, the reaction zone generally is not allowed to fill up with liquid resulting in reduced retention times in the reaction zone. Substantially higher ultimate yields of the preferred DMN isomer and reductions in the amounts of side reaction products and coke or heavy material lay downs on the catalyst result from this operation. Typically, trickle-bed down flow conditions can be maintained through reactor design and regulation of process parameters to prevent undue accumulations of liquids within the reaction zone and to control the space velocities through the reaction zone at values which result in optimum yields and product distributions.

The following examples present, in certain instances, preferred embodiments of the present invention and are not to be used to unduly limit the scope of the appended claims.

EXAMPLE I

In this example, a catalyst having about 40 weight per cent hydrogen form mordenite in a gamma alumina matrix was produced.

A quantity of hydrogen form mordenite powder (Zeolon 200 produced by Norton Company) was added to a sol of gamma alumina. The mixture was thoroughly mixed and then solidified by increasing its pH with ammonia. The resulting solid was dried and then extruded into 1/32 inch extrudate particles. The catalyst contained about 40 weight percent mordenite which was essentially 100 per cent decationized (the hydrogen form). This catalyst was termed "Catalyst A."

Another catalyst was made in a similar manner to that described above except that it contained only 2.4 weight per cent hydrogen mordenite in a gamma alumina matrix. This catalyst was termed "Catalyst B."

A third catalyst was prepared by forming 1/16 inch pellets out of 100 per cent of the Zeolon 200 molecular sieve material. This catalyst was termed "Catalyst C."

EXAMPLE II

In this example, a comparison was made for the isomerization properties of the three catalysts prepared as described in Example I above.

A one inch (I.D.) reactor was placed in a salt bath in a vertical position. The reactor system was designed so that liquid feed together with gaseous hydrogen would first pass through a preheater located above the reactor and then flow down through the reactor for reaction and eventual recovery as product. The reaction conditions were regulated so the flow of feed through the reactor was in a down flow trickle-bed operation. Previous experience with liquid full reactors in which the feed was up flow indicated reduced performance in that mode.

Conversion of 1,5-dimethylnaphthalene as used in these examples is defined as the weight of 1,5-dimethylnaphthalene which disappeared divided by the weight of 1,5-dimethylnaphthalene in the feed, the reported value expressed in per cent. Yield of 2,6-dimethylnaphthalene is defined as the weight of 2,6-dimethylnaphthalene produced per weight of 1,5-dimethylnaphthalene in the feed expressed as a per cent value. The selectivity to 2,6-dimethylnaphthalene is the product of (yield) (1/conversion) represented in percentage terms as the weight of 2,6-dimethylnaphthalene produced per weight of 1,5-dimethylnaphthalene in the feed which disappeared.

The results of the above testing are reported in the following tables. The crude feed is shown as Run O.

TABLE I

| Run No. | 0 | 1 | 2 | 3 | 4 | 5 | 6 | 7 |
|---|---|---|---|---|---|---|---|---|
| Reaction Conditions | | | | | | | | |
| Salt Bath Temperature (° C) | — | 300 | 300 | 300 | 300 | 300 | 300 | 300 |
| Catalyst Type | — | B | B | B | B | C | C | C |
| Catalyst Weight (g) | — | 80 | 80 | 80 | 80 | 100 | 100 | 100 |

TABLE I-continued

| Run No. | 0 | 1 | 2 | 3 | 4 | 5 | 6 | 7 |
|---|---|---|---|---|---|---|---|---|
| Crude 1,5-DMN Feed Flow Rate (g/hr.) | — | 22.4 | 22.4 | 22.4 | 22.4 | 22.0 | 22.0 | 22.0 |
| Crude 1,5-DMN Feed WHSV (hr$^{-1}$) | — | 0.28 | 0.28 | 0.28 | 0.28 | 0.22 | 0.22 | 0.22 |
| Hydrogen Feed Flow Rate (l/hr.) | — | 0.51 | 0.51 | 0.51 | 0.51 | 0.60 | 0.60 | 0.60 |
| Hydrogen Feed/Crude 1,5-DMN Feed Mole Ratio | — | 0.15 | 0.15 | 0.15 | 0.15 | 0.18 | 0.18 | 0.18 |
| Pressure (psig) | — | 50 | 50 | 50 | 50 | 50 | 50 | 50 |
| Catalyst Time on Stream (hrs.) | — | 4 | 5.3 | 21.3 | 22.8 | 7.5 | 19.5 | 20.5 |
| Analysis of Products wt. % | | | | | | | | |
| Other Lower Boiling Components | 3.32 | 14.0 | 9.44 | 5.25 | 5.44 | 7.87 | 5.99 | 5.52 |
| 2-Methylnaphthalene | 0.06 | 1.69 | 1.59 | 0.71 | 0.54 | 4.18 | 2.12 | 1.52 |
| 1-Methylnaphthalene | 1.16 | 0.77 | 0.70 | 0.48 | 0.56 | 1.78 | 1.16 | 1.07 |
| Ethylnaphthalene (isomer not known) | 0.06 | 0.04 | 0.05 | 0.00 | 0.04 | 0.00 | 0.06 | 0.00 |
| 2,6-Dimethylnaphthalene | 0.00 | 30.9 | 35.2 | 27.1 | 18.8 | 28.8 | 28.0 | 27.5 |
| 2,7-Dimethylnaphthalene | 0.00 | 1.17 | 1.39 | 0.57 | 0.43 | 5.03 | 1.96 | 1.33 |
| 1,6-Dimethylnaphthalene | 1.50 | 25.3 | 33.1 | 27.4 | 20.5 | 28.0 | 27.9 | 25.0 |
| 1,7-Dimethylnaphthalene | 0.00 | 0.62 | 0.65 | 0.00 | 0.00 | 3.14 | 1.19 | 0.65 |
| 1,5-Dimethylnaphthalene | 89.5 | 25.0 | 17.0 | 38.3 | 53.3 | 14.0 | 27.1 | 35.3 |
| 1,8-Dimethylnaphthalene | 0.59 | 0.07 | 0.12 | 0.00 | 0.00 | 0.25 | 0.07 | 0.29 |
| Trimethylnaphthalenes | 0.00 | 0.44 | 0.57 | 0.00 | 0.00 | 4.76 | 2.28 | 0.68 |
| Higher Boiling Components | 0.00 | 0.03 | 0.16 | 0.13 | 0.30 | 2.19 | 2.27 | 1.24 |
| Calculations | | | | | | | | |
| Conversion of 1,5-DMN (wt. %) | — | 72.1 | 81.0 | 57.2 | 40.4 | 84.4 | 69.7 | 60.6 |
| Yield of 2,6-DMN (wt. %) | — | 34.5 | 39.3 | 30.3 | 21.0 | 32.2 | 31.3 | 30.7 |
| Selectivity to 2,6-DMN (wt. %) | — | 47.9 | 48.5 | 52.9 | 52.0 | 38.1 | 44.9 | 50.7 |

TABLE II

| Run No. | 8 | 9 | 10 | 11 | 12 | 13 | 14 |
|---|---|---|---|---|---|---|---|
| Reaction Conditions | | | | | | | |
| Salt Bath Temperature (° C) | 300 | 300 | 300 | 300 | 300 | 300 | 300 |
| Catalyst Type | A | A | A | A | A | A | A |
| Catalyst Weight (g) | 80 | 80 | 80 | 80 | 80 | 80 | 80 |
| Crude 1,5-DMN Feed Flow Rate (g/hr.) | 20.1 | 20.1 | 20.0 | 20.0 | 20.0 | 56 | 56 |
| Crude 1,5-DMN Feed WHSV (hr—) | 0.25 | 0.25 | 0.25 | 0.25 | 0.25 | 0.70 | 0.70 |
| Hydrogen Feed Flow Rate (l/hr.) | 0.62 | 0.62 | 0.62 | 0.62 | 0.62 | 0.62 | 0.62 |
| Hydrogen Feed/Crude 1,5-DMN Feed Mole Ratio | 0.20 | 0.20 | 0.20 | 0.20 | 0.20 | 0.07 | 0.07 |
| Pressure (psig) | 50 | 50 | 50 | 50 | 50 | 50 | 50 |
| Catalyst Time on Stream (hrs.) | 18 | 19 | 41 | 42.5 | 66 | 69 | 71 |
| Analysis of Products wt. % | | | | | | | |
| Other Lower Boiling Components | 5.95 | 5.95 | 5.67 | 5.34 | 5.73 | 5.91 | 6.11 |
| 2-Methylnaphthalene | 3.26 | 2.56 | 2.24 | 2.06 | 1.96 | 1.05 | 1.02 |
| 1-Methylnaphthalene | 1.38 | 1.04 | 0.93 | 0.84 | 0.80 | 0.46 | 0.46 |
| Ethylnaphthalene (isomer not known) | 0.04 | 0.00 | 0.05 | 0.00 | 0.00 | 0.00 | 0.00 |
| 2,6-Dimethylnaphthalene | 38.2 | 42.3 | 43.5 | 43.5 | 42.1 | 39.9 | 39.4 |
| 2,7-Dimethylnaphthalene | 2.47 | 1.90 | 1.58 | 1.53 | 1.46 | 0.81 | 0.78 |
| 1,6-Dimethylnaphthalene | 35.3 | 34.9 | 35.6 | 36.1 | 35.7 | 34.1 | 34.1 |
| 1,7-Dimethylnaphthalene | 1.66 | 1.02 | 0.67 | 0.94 | 0.89 | 0.23 | 0.23 |
| 1,5-Dimethylnaphthalene | 6.39 | 6.80 | 6.46 | 6.97 | 6.85 | 16.3 | 17.7 |
| 1,8-Dimethylnaphthalene | 0.11 | 0.15 | 0.06 | 0.05 | 0.09 | 0.00 | 0.00 |
| Trimethylnaphthalenes | 3.23 | 1.96 | 1.63 | 1.10 | 2.75 | 0.10 | 0.10 |
| Higher Boiling Components | 2.03 | 1.36 | 1.73 | 1.55 | 1.73 | 1.21 | 0.14 |
| Calculations | | | | | | | |
| Conversion of 1,5-DMN (wt. %) | 92.9 | 92.4 | 92.8 | 92.2 | 92.3 | 81.8 | 80.2 |
| Yield of 2,6-DMN (wt. %) | 42.7 | 47.3 | 48.6 | 48.6 | 47.0 | 44.6 | 44.0 |
| Selectivity to 2,6-DMN (wt. %) | 46.0 | 51.2 | 52.4 | 52.7 | 51.0 | 54.5 | 54.9 |

TABLE III

| Run No. | 15 | 16 | 17 | 18 | 19 | 20 | 21 | 22 |
|---|---|---|---|---|---|---|---|---|
| Reaction Conditions | | | | | | | | |
| Salt Bath Temperature (° C) | 300 | 300 | 300 | 320 | 320 | 320 | 330 | 330 |
| Catalyst Type | A | A | A | A | A | A | A | A |
| Catalyst Weight (g) | 80 | 80 | 80 | 80 | 80 | 80 | 80 | 80 |
| Crude 1,5-DMN Feed Flow Rate (g/hr.) | 56 | 56 | 56 | 56 | 56 | 56 | 56 | 56 |
| Crude 1,5-DMN Feed WHSV (hr$^{-1}$) | 0.70 | 0.70 | 0.70 | 0.70 | 0.70 | 0.70 | 0.70 | 0.70 |
| Hydrogen Feed Flow Rate (l/hr.) | 0.62 | 0.62 | 0.62 | 0.62 | 0.62 | 0.62 | 0.62 | 0.62 |
| Hydrogen Feed/Crude 1,5-DMN Feed Mole Ratio | 0.07 | 0.07 | 0.07 | 0.07 | 0.07 | 0.07 | 0.07 | 0.07 |
| Pressure (psig) | 50 | 50 | 50 | 50 | 50 | 50 | 50 | 50 |
| Catalyst Time on Stream (hrs.) | 73 | 89.5 | 91.0 | 92.3 | 93.8 | 95.3 | 100 | 101 |
| Analysis of Products wt. % | | | | | | | | |
| Other Lower Boiling Components | 5.87 | 5.41 | 6.44 | 6.44 | 5.44 | 5.15 | 5.40 | 4.44 |
| 2-Methylnaphthalene | 0.95 | 0.83 | 0.75 | 0.78 | 1.12 | 1.18 | 1.74 | 2.66 |
| 1-Methylnaphthalene | 0.44 | 0.47 | 0.52 | 0.50 | 0.50 | 0.53 | 0.72 | 1.09 |
| Ethylnaphthalene (isomer not known) | 0.00 | 0.04 | 0.00 | 0.05 | 0.08 | 0.04 | 0.00 | 0.04 |
| 2,6-Dimethylnaphthalene | 39.0 | 34.2 | 27.9 | 28.4 | 39.5 | 41.6 | 42.8 | 41.5 |
| 2,7-Dimethylnaphthalene | 0.76 | 0.59 | 0.42 | 0.67 | 1.01 | 1.02 | 1.34 | 2.23 |
| 1,6-Dimethylnaphthalene | 32.7 | 28.9 | 27.6 | 28.7 | 36.1 | 35.9 | 37.2 | 35.2 |
| 1,7-Dimethylnaphthalene | 0.22 | 0.00 | 0.00 | 0.00 | 0.00 | 0.38 | 0.67 | 1.43 |
| 1,5-Dimethylnaphthalene | 19.3 | 29.1 | 35.9 | 34.0 | 15.5 | 13.1 | 7.84 | 6.87 |
| 1,8-Dimethylnaphthalene | 0.00 | 0.00 | 0.00 | 0.00 | 0.00 | 0.00 | 0.00 | 0.10 |
| Trimethylnaphthalenes | 0.12 | 0.00 | 0.03 | 0.08 | 0.11 | 0.24 | 0.74 | 3.53 |
| Higher Boiling Components | 0.72 | 0.00 | 0.44 | 0.47 | 0.62 | 0.86 | 1.56 | 0.95 |

TABLE III-continued

| Run No. | 15 | 16 | 17 | 18 | 19 | 20 | 21 | 22 |
|---|---|---|---|---|---|---|---|---|
| Calculations | | | | | | | | |
| Conversion of 1,5-DMN (wt. %) | 78.4 | 67.5 | 59.9 | 62.0 | 82.7 | 85.4 | 91.2 | 92.3 |
| Yield of 2,6-DMN (wt. %) | 43.6 | 38.2 | 31.2 | 31.7 | 44.1 | 46.5 | 47.8 | 46.4 |
| Selectivity of 2,6-DMN (wt. %) | 55.6 | 56.6 | 52.1 | 51.2 | 53.4 | 54.4 | 52.4 | 50.2 |

EXAMPLE III

In this example, catalyst A as described in Example I above, was tested under reaction conditions in which the feed was either passed under down flow (trickle-bed) or up flow (liquid-fill) conditions. The reaction system was similar to that described in Example II except that in certain instances a ½ inch I.D. reactor was substituted for the one inch I.D. unit normally used. Reactor type A signifies 1 inch nominal I.D. while type B refers to nominal ½ inch I.D. unit. Reactor mode D refers to down flow (trickle-bed) of feed where there was essentially no accumulation of liquid in the reactor while mode U refers to up flow (liquid-fill) conditions in which feedstock enters the reactor at its bottom and flows upwards. There is a large accumulation of feedstock in the reactor under this condition. Catalyst type R refers to catalyst which had been used in previous isomerization studies but had been successfully regenerated while Catalyst type F is a fresh catalyst. Both were produced as described in Example I for catalyst A. The reactor was recharged with the catalyst type described for Runs 30, 33, 36 and 38 of the table below.

TABLE IV

| Run No. | 0 | 23 | 24 | 25 | 26 | 27 | 28 | 29 |
|---|---|---|---|---|---|---|---|---|
| Reaction Conditions | | | | | | | | |
| Reactor Type | — | A | A | A | A | A | A | |
| Reactor Operation Mode | — | D | D | D | D | D | D | |
| Salt Bath Temperature (° C) | — | 300 | 300 | 300 | 300 | 300 | 300 | |
| Catalyst Type | — | R | R | R | R | R | R | |
| Catalyst Weight (g) | — | 80 | 80 | 80 | 80 | 80 | 80 | |
| Crude 1,5-DMN Feed Flow Rate (g/hr.) | — | 15 | 20 | 19.5 | 30 | 29 | 34 | |
| Crude 1,5-DMN Feed WHSV (hr.$^{-1}$) | — | 0.19 | 0.25 | 0.24 | 0.38 | 0.36 | 0.43 | |
| Hydrogen Feed Flow Rate (l/hr.) | — | 0.62 | 0.62 | 0.62 | 0.62 | 0.62 | 0.62 | |
| Hydrogen Feed/Crude 1,5-DMN Feed Mole Ratio | — | 0.26 | 0.20 | 0.21 | 0.13 | 0.14 | 0.12 | |
| Pressure (psig) | — | 50 | 50 | 50 | 50 | 50 | 50 | |
| Catalyst Time on Stream (hrs.) | — | 22 | 45 | 69 | 94 | 163 | 187 | |
| Analysis of Products | | | | | | | | |
| Other Lower Boiling Components | 6.46 | 6.37 | 6.50 | 5.72 | 5.39 | 5.13 | 5.28 | |
| 2-Methylnaphthalene | 0.06 | 4.15 | 3.55 | 3.26 | 2.69 | 2.22 | 2.04 | |
| 1-Methylnaphthalene | 3.13 | 1.70 | 1.45 | 1.30 | 1.09 | 0.99 | 1.08 | |
| Ethylnaphthalene (isomer not known) | 0.00 | 0.02 | 0.01 | 0.03 | 0.00 | 0.03 | 0.03 | |
| 2,6-Dimethylnaphthalene | 0.03 | 39.5 | 39.5 | 41.7 | 43.2 | 40.0 | 35.0 | |
| 2,7-Dimethylnaphthalene | 0.04 | 2.43 | 2.00 | 1.70 | 1.07 | 0.74 | 0.60 | |
| 1,6-Dimethylnaphthalene | 1.90 | 34.6 | 36.3 | 36.2 | 36.9 | 35.0 | 32.9 | |
| 1,7-Dimethylnaphthalene | 0.00 | 1.52 | 0.72 | 0.70 | 0.48 | 0.52 | 0.34 | |
| 1,5-Dimethylnaphthalene | 88.0 | 6.05 | 6.39 | 6.29 | 7.56 | 14.3 | 21.8 | |
| 1,8-Dimethylnaphthalene | 0.34 | 0.09 | 0.08 | 0.05 | 0.00 | 0.01 | 0.00 | |
| Trimethylnaphthalenes | 0.00 | 2.61 | 2.40 | 2.03 | 0.45 | 0.21 | 0.10 | |
| Higher Boiling Components | 0.00 | 0.82 | 1.06 | 0.94 | 1.07 | 0.90 | 0.76 | |
| Calculations | | | | | | | | |
| Conversion of 1,5-DMN (wt. %) | — | 93.1 | 92.7 | 92.9 | 91.4 | 83.8 | 75.2 | |
| Yield of 2,6-DMN (wt. %) | — | 44.9 | 44.9 | 47.4 | 49.1 | 45.5 | 39.8 | |
| Selectivity of 2,6-DMN (wt. %) (yield/conversion ×100) | — | 48.2 | 48.4 | 51.0 | 53.7 | 54.3 | 52.9 | |

TABLE V

| Run No. | 30 | 31 | 32 | 33 | 34 | 35 |
|---|---|---|---|---|---|---|
| Reaction Conditions | | | | | | |
| Reactor Type | A | A | A | A | A | A |
| Reactor Operation Mode | D | D | D | D | D | D |
| Salt Bath Temperature (° C) | 300 | 300 | 300 | 300 | 300 | 300 |
| Catalyst Type | F | F | F | F | F | F |
| Catalyst Weight (g) | 80 | 80 | 80 | 80 | 80 | 80 |
| Crude 1,5-DMN Feed Flow Rate (g/hr.) | 36 | 30 | 35 | 28 | 28 | 28 |
| Crude 1,5-DMN Feed WHSV (hr.$^{-1}$) | 0.44 | 0.38 | 0.44 | 0.35 | 0.35 | 0.35 |
| Hydrogen Feed Flow Rate (l/hr.) | 0.62 | 0.62 | 0.62 | 0.6 | 0.6 | 0.6 |
| Hydrogen Feed/Crude 1,5-DMN Feed Mole Ratio | 0.11 | 0.13 | 0.11 | 0.1 | 0.1 | 0.1 |
| Pressure (psig) | 50 | 50 | 50 | 185 | 185 | 185 |
| Catalyst Time on Stream (hrs.) | 18 | 42 | 66 | 18.5 | 42.5 | 66.5 |
| Analysis of Products | | | | | | |
| Other Lower Boiling Components | 5.38 | 4.99 | 4.85 | 6.06 | 5.43 | 5.16 |
| 2-Methylnaphthalene | 2.75 | 2.56 | 2.17 | 3.00 | 2.43 | 1.89 |
| 1-Methylnaphthalene | 1.13 | 1.07 | 1.00 | 1.21 | 1.03 | 1.12 |
| Ethylnaphthalene (isomer not known) | 0.02 | 0.02 | 0.03 | 0.03 | 0.03 | 0.03 |
| 2,6-Dimethylnaphthalene | 41.9 | 40.6 | 37.8 | 41.5 | 41.9 | 32.9 |
| 2,7-Dimethylnaphthalene | 1.10 | 0.95 | 0.67 | 1.20 | 0.73 | 0.51 |
| 1,6-Dimethylnaphthalene | 36.7 | 37.9 | 35.9 | 35.7 | 35.0 | 31.1 |
| 1,7-Dimethylnaphthalene | 0.77 | 0.69 | 0.51 | 0.7 | 0.00 | 0.00 |
| 1,5-Dimethylnaphthalene | 8.15 | 9.65 | 16.1 | 7.7 | 12.2 | 26.5 |
| 1,8-Dimethylnaphthalene | 0.04 | 0.00 | 0.02 | 0.03 | 0.00 | 0.00 |
| Trimethylnaphthalenes | 0.57 | 0.35 | 0.14 | 0.99 | 0.39 | 0.10 |

TABLE V-continued

| Run No. | 30 | 31 | 32 | 33 | 34 | 35 |
|---|---|---|---|---|---|---|
| Higher Boiling Components | 1.47 | 1.17 | 0.84 | 1.87 | 0.80 | 0.72 |
| Calculations | | | | | | |
| Conversion of 1,5-DMN (wt. %) | 90.7 | 89.0 | 81.7 | 91 | 86.1 | 69.9 |
| Yield of 2,6-DMN (wt. %) | 47.6 | 46.1 | 43.0 | 47.2 | 47.6 | 37.4 |
| Selectivity of 2,6-DMN (wt. %) (yield/conversion X100) | 52.5 | 51.8 | 52.6 | 52 | 55.3 | 53.5 |

TABLE VI

| Run No. | 36 | 37 | 38 | 39 |
|---|---|---|---|---|
| Reaction Conditions | | | | |
| Reactor Type | B | B | B | B |
| Reactor Operation Mode | U | U | U | U |
| Salt Bath Temperature (° C) | 300 | 300 | 300 | 300 |
| Catalyst Type | F | F | F | F |
| Catalyst Weight (g) | 20 | 20 | 20 | 20 |
| Crude 1,5-DMN Feed Flow Rate (g/hr.) | 20 | 20.5 | 10 | 10 |
| Crude 1,5-DMN Feed WHSV (hr.$^{-1}$) | 1.0 | 1.0 | 0.5 | 0.5 |
| Hydrogen Feed Flow Rate (l/hr.) | — | — | — | — |
| Hydrogen Feed/Crude 1,5-DMN Feed Mole Ratio | — | — | — | — |
| Pressure (psig) | 50 | 50 | 50 | 50 |
| Catalyst Time on Stream (hrs.) | 5 | 6 | 23 | |
| Analysis of Products | | | | |
| Other Lower Boiling Components | 4.56 | 4.17 | 4.29 | 4.41 |
| 2-Methylnaphthalene | 3.37 | 0.23 | 3.92 | 1.69 |
| 1-Methylnaphthalene | 1.41 | 2.44 | 1.82 | 1.60 |
| Ethylnaphthalene (isomer not known) | 0.00 | 0.05 | 0.01 | 0.03 |
| 2,6-Dimethylnaphthalene | 39.6 | 1.67 | 35.7 | 20.7 |
| 2,7-Dimethylnaphthalene | 1.85 | 0.08 | 2.62 | 0.61 |
| 1,6-Dimethylnaphthalene | 35.7 | 4.49 | 31.6 | 24.5 |
| 1,7-Dimethylnaphthalene | 0.85 | 0.00 | 1.24 | 0.00 |
| 1,5-Dimethylnaphthalene | 7.94 | 85.4 | 12.6 | 45.3 |
| 1,8-Dimethylnaphthalene | 0.07 | 0.16 | 0.13 | 0.00 |
| Trimethylnaphthalenes | 1.89 | 0.04 | 3.30 | 0.01 |
| Higher Boiling Components | 2.62 | 1.23 | 2.56 | 1.04 |
| Calculations | | | | |
| Conversion of 1,5-DMN (wt. %) | 91.0 | 3.0 | 85.7 | 48.5 |
| Yield of 2,6-DMN (wt. %) | 45.0 | 1.9 | 40.6 | 23.5 |
| Selectivity to 2,6-DMN (wt. %) (yield/conversion X100) | 49.5 | 63 | 47.4 | 48.5 |

As is illustrated in the data shown above, the down flow (trickle-bed) operations were consistently higher in yields of 2,6-dimethylnaphthalene than the up flow (liquid-full) mode of operations.

EXAMPLE IV

In this example, catalyst A of Example I was tested in a reactor system similar to that described in Example II except that gas phase isomerization operations were maintained. The catalyst was changed after Run 44 was completed.

The data collected are shown in the tables below.

TABLE VII

| Run No. | 0 | 40 | 41 | 42 | 43 | 44 |
|---|---|---|---|---|---|---|
| Reaction Conditions | | | | | | |
| Salt Bath Temperature (° C) | — | 300 | 300 | 300 | 300 | 300 |
| Catalyst Type | — | A | A | A | A | A |
| Catalyst Weight (g) | — | 80 | 80 | 80 | 80 | 80 |
| Crude 1,5-DMN Feed Flow Rate (g/hr.) | — | 20.0 | 20.0 | 20.0 | 20.0 | 20.0 |
| Crude 1,5-DMN Feed WHSV (hr.$^{-1}$) | — | 0.25 | 0.25 | 0.25 | 0.25 | 0.25 |
| Hydrogen Feed Flow Rate (l/hr.) | — | 6.2 | 6.2 | 6.2 | 6.2 | 6.2 |
| Hydrogen Feed/Crude 1,5-DMN Feed Mole Ratio | — | 2.0 | 2.0 | 2.0 | 2.0 | 2.0 |
| Pressure (psig) | — | 0 | 0 | 0 | 0 | 0 |
| Catalyst Time on Stream (hrs.) | — | 2 | 4.5 | 6.5 | 22.5 | 24 |
| Analysis of Products | | | | | | |
| Other Lower Boiling Components | 3.32 | 15.36 | 8.13 | 5.30 | 5.16 | 6.13 |
| 2-Methylnaphthalene | 0.06 | 2.87 | 1.84 | 1.61 | 1.13 | 0.97 |
| 1-Methylnaphthalene | 1.16 | 1.15 | 0.70 | 0.60 | 0.47 | 0.51 |
| Ethylnaphthalene (isomer not known) | 0.06 | 0.00 | 0.04 | 0.04 | 0.00 | 0.05 |
| 2,6-Dimethylnaphthalene | 0.00 | 34.8 | 42.4 | 44.9 | 42.1 | 35.6 |
| 2,7-Dimethylnaphthalene | 0.00 | 3.29 | 2.14 | 1.67 | 1.14 | 0.90 |
| 1,6-Dimethylnaphthalene | 1.50 | 30.3 | 35.3 | 36.9 | 36.2 | 33.2 |
| 1,7-Dimethylnaphthalene | 0.00 | 2.49 | 1.42 | 1.02 | 0.48 | 0.28 |
| 1,5-Dimethylnaphthalene | 89.5 | 5.48 | 6.36 | 6.89 | 13.0 | 22.2 |
| 1,8-Dimethylnaphthalene | 0.59 | 0.00 | 0.00 | 0.00 | 0.00 | 0.00 |
| Trimethylnaphthalenes | 0.00 | 3.99 | 1.46 | 1.02 | 0.31 | 0.18 |
| Higher Boiling Components | 0.00 | 0.23 | 0.13 | 0.00 | 0.01 | 0.04 |
| Calculations | | | | | | |
| Conversion of 1,5-DMN (wt. %) | — | 93.9 | 92.9 | 92.3 | 85.5 | 75.2 |
| Yield of 2,6-DMN (wt. %) | — | 38.9 | 47.4 | 50.2 | 47.0 | 39.8 |

TABLE VII-continued

| Run No. | 0 | 40 | 41 | 42 | 43 | 44 |
|---|---|---|---|---|---|---|
| Selectivity of 2,6-DMN (wt. %) (yield/conversion X100) | — | 41.4 | 51.0 | 54.4 | 55.0 | 52.9 |

TABLE VIII

| Run No. | 45 | 46 | 47 | 48 | 49 | 50 |
|---|---|---|---|---|---|---|
| Reaction Conditions | | | | | | |
| Salt Bath Temperature (° C) | 300 | 300 | 310 | 310 | 330 | 330 |
| Catalyst Type | A | A | A | A | A | A |
| Catalyst Weight (g) | 80 | 80 | 80 | 80 | 80 | 80 |
| Crude 1,5-DMN Feed Flow Rate (g/hr.) | 40.0 | 40.0 | 40.0 | 40.0 | 40.0 | 40.0 |
| Crude 1,5-DMN Feed WHSV (hr.$^{-1}$) | 0.50 | 0.50 | 0.50 | 0.50 | 0.50 | 0.50 |
| Hydrogen Feed Flow Rate (l/hr.) | 12.4 | 12.4 | 12.4 | 12.4 | 12.4 | 12.4 |
| Hydrogen Feed/Crude 1,5-DMN Feed Mole Ratio | 2.0 | 2.0 | 2.0 | 2.0 | 2.0 | 2.0 |
| Pressure (psig) | 0 | 0 | 0 | 0 | 0 | 0 |
| Catalyst Time on Stream (hrs.) | 4.5 | 5.3 | 28.3 | 29.3 | 50 | 51.3 |
| Analysis of Products | | | | | | |
| Other Lower Boiling Components | 5.31 | 5.62 | 5.26 | 5.73 | 5.20 | 5.56 |
| 2-Methylnaphthalene | 1.85 | 1.31 | 0.97 | 0.78 | 0.61 | 0.37 |
| 1-Methylnaphthalene | 0.70 | 0.51 | 0.44 | 0.51 | 0.57 | 0.84 |
| Ethylnaphthalene (isomer not known) | 0.00 | 0.00 | 0.04 | 0.05 | 0.05 | 0.05 |
| 2,6-Dimethylnaphthalene | 44.1 | 43.4 | 41.3 | 34.5 | 25.8 | 10.8 |
| 2,7-Dimethylnaphthalene | 1.68 | 1.28 | 0.94 | 0.52 | 0.68 | 0.37 |
| 1,6-Dimethylnaphthalene | 37.0 | 37.5 | 34.3 | 29.0 | 25.6 | 15.4 |
| 1,7-Dimethylnaphthalene | 1.09 | 0.60 | 0.35 | 0.00 | 0.00 | 0.00 |
| 1,5-Dimethylnaphthalene | 6.95 | 8.98 | 16.1 | 28.8 | 41.3 | 66.6 |
| 1,8-Dimethylnaphthalene | 0.00 | 0.34 | 0.00 | 0.00 | 0.08 | 0.00 |
| Trimethylnaphthalenes | 1.32 | 0.39 | 0.24 | 0.16 | 0.14 | 0.00 |
| Higher Boiling Components | 0.01 | 0.01 | 0.01 | 0.02 | 0.02 | 0.03 |
| Calculations | | | | | | |
| Conversion of 1,5-DMN (wt. %) | 92.2 | 90.0 | 82.0 | 67.8 | 53.9 | 25.6 |
| Yield of 2,6-DMN (wt. %) | 49.3 | 48.5 | 46.1 | 38.5 | 28.8 | 12.1 |
| Selectivity to 2,6-DMN (wt. %) (yield/conversion X100) | 53.5 | 53.9 | 56.2 | 56.8 | 53.4 | 47.1 |

We claim as our invention:

1. A method for isomerization of dimethylnaphthalenes including conversion of a feed containing 1,5-dimethylnaphthalene to 1,6 and 2,6-dimethylnaphthalenes, the process comprising contacting said feed at isomerization conditions with a catalyst consisting essentially of from about 35 to about 45 weight percent of mordenite in the hydrogen form dispersed in a gamma alumina matrix, to effect the production of said 1,6 and 2,6-dimethylnaphthalenes.

2. The method of claim 1 further characterized in that said mordenite has above about 90 weight percent of its ion exchangeable cations replaced with hydrogen ions.

3. The method of claim 2 further characterized in that above about 95 weight percent of the ion exchangeable cations are replaced with hydrogen ions.

4. The method of claim 1 further characterized in that said catalyst comprises about 60 weight percent gamma alumina.

5. The method of claim 1 further characterized in that said isomerization conditions include contacting said feed together with hydrogen in the vapor phase with said catalyst.

6. The method of claim 1 further characterized in that said isomerization conditions include contacting said feed in the liquid phase with said catalyst.

7. The method of claim 1 further characterized in that isomerization conditions include a temperature in the range of from about 200° to about 400° C and a pressure in the range of from about 10 to about 1500 p.s.i.g.

8. A method for isomerization of dimethylnaphthalene including conversion of a feed containing 1,5-dimethylnaphthalene to 1,6 and 2,6-dimethylnaphthalene isomers, the process comprising contacting said feed at isomerization conditions including the presence of gaseous hydrogen and liquid feed with catalyst consisting essentially of from about 35 to about 45 weight percent mordenite in the hydrogen form dispersed in a gamma alumina matrix, to effect the production of said 1,6 and 2,6-dimethylnaphthalenes.

9. The method of claim 8 further characterized in that alumina is the gamma from and said mordenite has above 95 weight percent of its ion exchangeable metal cations replaced with hydrogen ions.

10. The method of claim 8 further characterized in that said isomerization conditions include a temperature in the range of from about 250° to about 350° C.

11. The method of claim 8 further characterized in that said mordenite is about 40 weight percent of the catalyst.

* * * * *